United States Patent
Buffel et al.

(10) Patent No.: US 9,458,117 B2
(45) Date of Patent: Oct. 4, 2016

(54) PROCESS FOR PRODUCING 1,4,7,10-TETRAAZACYCLODODECANE-1,4,7,10-TETRAACETIC ACID AND COMPLEXES THEREOF

(71) Applicant: Agfa HealthCare NV, Mortsel (BE)

(72) Inventors: Diederik Buffel, Mortsel (BE); Rakesh Ganorkar, Mortsel (BE); Jennifer Burt, Mortsel (BE); Xavier Boi, Mortsel (BE)

(73) Assignee: AGFA HEALTHCARE NV, Mortsel (BE)

( * ) Notice: Subject to any disclaimer, the term of this patent is extended or adjusted under 35 U.S.C. 154(b) by 0 days.

(21) Appl. No.: 14/763,550

(22) PCT Filed: Jan. 22, 2014

(86) PCT No.: PCT/EP2014/051217
§ 371 (c)(1),
(2) Date: Jul. 27, 2015

(87) PCT Pub. No.: WO2014/114664
PCT Pub. Date: Jul. 31, 2014

(65) Prior Publication Data
US 2016/0024030 A1    Jan. 28, 2016

Related U.S. Application Data

(60) Provisional application No. 61/758,289, filed on Jan. 30, 2013.

(30) Foreign Application Priority Data
Jan. 28, 2013 (EP) .................................... 13152873

(51) Int. Cl.
C07D 257/02 (2006.01)
C07D 457/04 (2006.01)
A61K 49/10 (2006.01)

(52) U.S. Cl.
CPC ........... *C07D 257/02* (2013.01); *A61K 49/108* (2013.01); *C07D 457/04* (2013.01)

(58) Field of Classification Search
None
See application file for complete search history.

(56) References Cited

FOREIGN PATENT DOCUMENTS

| CN | 1130189 A | 9/1996 |
|---|---|---|
| CN | 102659702 A | 9/2012 |
| WO | 99/05128 A1 | 2/1999 |

OTHER PUBLICATIONS

Official Communication issued in International Patent Application No. PCT/EP2014/051217, mailed on Feb. 25, 2014.
Stetter et al., "Complex Formation with Tetraazacycloalkane-N,N',N",N'"—Tetraacetic Acids as a Function of Ring Size," Angew. Chem. Int. Ed. Engl., vol. 15, No. 11, 1976, 1 page.
Delgado et al., "Metal Complexes of Cyclic Tetra-Azatetra-Acetic Acids," Talanta, vol. 29, 1982, pp. 815-822.
Desreux, "Nuclear Magnetic Resonance Spectroscopy of Lanthanide Complexes with a Tetraacetic Tetraaza Macrocycle, Unusual Conformation Properties," Inorg. Chem. vol. 19, No. 5, 1980, pp. 1319-1324.
Clarke et al., "Stabilities of the Alkaline Earth and Divalent Transition Metal Complexes of the Tetraazamacrocyclic Tetraacetic Acid Ligands," Inorganica Chimica Acta, 190, 1991, pp. 27-36.
Chang et al., "Synthesis, Characterization, and Crystal Structures of M(DO3A) (M=Fe,Gd) and Na[M(DOTA)] (M=Fe, Y,Gd)," Inorg. Chem. 32, 1993, pp. 3501-3508.

*Primary Examiner* — Noble Jarrell
(74) *Attorney, Agent, or Firm* — Keating and Bennett, LLP

(57) ABSTRACT

A process for producing 1,4,7,10-tetraazacyclododecane-1, 4,7,10-tetraacetic acid (DOTA) including salts and hydrates thereof of general formula (I) from the respective cyclen.

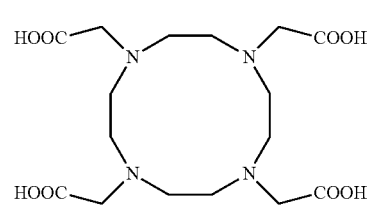

Formula (I)

The process involves the use of cationic- and anionic exchange resins and solvent treatments to remove the organic and inorganic contaminants. Any cations present in the raw DOTA or other contaminants resulting from the reaction of cyclen are largely reduced in early stages of the process allowing to obtain good yields of DOTA in a purified grade and in an easier and reliable way. The process is useful for the production of DOTA, of macrocyclic compounds including metal ions complexes thereof and of compositions including the macrocyclic compounds that can be used as contrast agents for magnetic resonance imaging.

10 Claims, No Drawings

PROCESS FOR PRODUCING 1,4,7,10-TETRAAZACYCLODODECANE-1,4,7,10-TETRAACETIC ACID AND COMPLEXES THEREOF

CROSS-REFERENCE TO RELATED APPLICATIONS

This application is a 371 National Stage Application of PCT/EP2014/051217, filed Jan. 22, 2014. This application claims the benefit of U.S. Provisional Application No. 61/758,289, filed Jan. 30, 2013, which is incorporated by reference herein in its entirety. In addition, this application claims the benefit of European Application No. 13152873.9, filed Jan. 28, 2013, which is also incorporated by reference herein in its entirety.

BACKGROUND OF THE INVENTION

1. Field of the Invention

The present invention relates to a process for producing 1,4,7,10-tetraazacyclododecane-1,4,7,10-tetraacetic acid (DOTA) including salts and hydrates thereof, macrocyclic compounds comprising metal ions complexes thereof and compositions comprising said macrocyclic compounds, which can be used to produce contrast agents for magnetic resonance imaging.

2. Description of the Related Art

Magnetic resonance imaging (MRI) is a powerful, non-invasive technique used to produce detailed two or three-dimensional anatomical images of tissues in the body. Conventional MRI uses the proton $^1H$ as its signal source which is highly abundant in tissues and it has the highest sensitivity of all the biologically relevant nuclei.

Contrast, which makes the differentiation of internal structures possible in the image, arises from how the signal decays and is the difference between the resulting signals from two tissue regions. The route by which the protons release the energy they absorbed from the radio-frequency pulse, thus reducing the transverse magnetisation and causing signal decay, is known as relaxation. In MRI two independent relaxation processes occur simultaneously: spin-lattice or longitudinal relaxation characterised by the time constant $T_1$, and spin-spin or transverse relaxation, characterised by the time constant $T_2$.

Often, when suitable $T_1$- or $T_2$-weighting sequences are used, the natural contrast between two tissues is enough to produce a diagnostically-useful image. However, some conditions do not lead to specific enough changes in the relaxation times of the affected tissue though and then a contrast agent is used to locally change the relaxation times of the diseased tissue, improving the image contrast.

Most contrast agents work by shortening the relaxation times of the water protons in the targeted tissue. $T_1$ contrast agents are based on paramagnetic metal ion chelates which make the tissue appear brighter on the $T_1$-weighted image (positive contrast). $T_2$ contrast agents are usually superparamagnetic iron oxide nanoparticles which create dark spots on the $T_2$-weighted image (negative contrast). $T_1$ agents are the most widely used and the majority of these are based on chelates of the gadolinium ion ($Gd^{3+}$).

To be an effective $T_1$ agent the gadolinium (III) chelate must significantly increase the proton relaxation rates in water. Gadolinium is the seventh element in the lanthanide series and, like the other lanthanide elements, it is most commonly found in the +3 oxidation state, corresponding to the electronic configuration $[Xe]4f^7$. This means that $Gd^{3+}$ has seven unpaired electrons, making it highly paramagnetic i.e. Gd(III) ions have large permanent magnetic moments (due to electron spin angular momentum), but in the absence of an external magnetic field these are randomly oriented. Due to its large size the Gd(III) ion typically has a coordination number of nine in its complexes. As a free ion gadolinium is very toxic for the tissues but is generally regarded as safe when administrated as a chelated compound.

The level of toxicity depends on the strength of the chelating agent, also known as ligand, chelator or sequestering agent.

Usually these ligands are organic compounds which form two or more separate coordinate bonds with a single central metal ion, in this case, the gadolinium ion, inactivating it thus reducing or eliminating its toxic effect in the tissues.

Polyaminopolycarboxylic acid compounds are the ligand type of choice because they form exceptionally stable complexes with the Gd(III) ion, which can be explained by a number of reasons. These compounds can be linear (such as pentetic acid or diethylene triamine pentaacetic acid also named as DTPA) or macrocyclic (such as 1,4,7,10-tetraazacyclododecane-1,4,7,10-tetraacetic acid, DOTA). DOTA is used as the ligand in the synthesis of the MRI contrast agent gadoterate meglumine ([Gd(DOTA)(H20)](meglumine)).

Several synthetic routes for the production of DOTA have been proposed, namely by Stetter, Hermann; Wolfram Frank (1976)—"Complex Formation with Tetraazacycloalkane-N, N',N",N'"; —tetraacetic Acids as a Function of Ring Size". Angewandte Chemie International Edition in English 15 (11): 686), by R. Delgado & J. J. Fraústo da Silva—Talanta, Vol. 29, pp. 815-822, Issue 10, 1982, and by J. F. Desreux—Inorg. Chem. 1980, 19, pp. 1319-1324.

The preparation of DOTA was first reported in 1976 by Stetter & Frank (full ref. above) through the reaction of 1,4,7,10-tetraazacyclododecane with chloroacetic acid in aqueous alkali medium to obtain DOTA wherein the resulting inorganic salts were separated and purified by treatment with an ion-exchange column Dowex 2×8.

The method most widely reported in the literature is typified by Delgado et al. (full ref. above), where cyclen is reacted with chloroacetic acid under aqueous basic conditions (pH =~10) to form DOTA, which is crystallised by acidifying the cooled DOTA solution to pH 2 with hydrochloric acid and placing it in the refrigerator overnight.

Desreux (full ref. above) also reported a similar procedure, but specified sodium hydroxide as being the base used, with a reaction temperature of 80° C., and stated that upon acidification DOTA precipitates out of solution at pH 2.5.

E. Clarke & A. Martel (1991)—Inorganica Chimica Acta, 190, pp 27-36), describes the preparation of DOTA by alkylation of cyclic tetraamine ligands with bromoacetic acid at a controlled pH between 11.2 to 11.3 being the resulting product recovered by treatment with a ion-exchange column as ammonium salts followed by treatment with a potassium cation solution at pH of 11.5 and vacuum concentration. The resulting ligands were then reprotonated by addition of HCl and isolated by recrystallization from hot water.

WO9905128 discloses a process for producing DOTA compounds by 2 step-alkylation wherein the alkylation agent is preferably bromoacetic acid but also includes chloroacetic acid, in aqueous solution at a basic pH with an excess of said alkylation agent, followed by hydrolysis and purification with ion exchange resins and with an optional recrystallization step in order to obtain highly purified DOTA compounds. In particular, WO9905128 discloses a multistep process for the preparation of DOTA starting from:

a) an alkylation reaction of a 2a,4a,6a,8a-decahydrotetraazacyclopent [fg]acenaphthylene with an acid in aqueous solution and at a basic pH, followed by b) a second alkylation reaction with a different alkylating agent, and by c) the hydrolisis of any ester groups, and wherein the amount of the first alkylating agent used in step a) varies between 2-2.3 mol of reagent per mol of substrate and from 2-3 mol in step b) and the reaction temperature varies from room temperature to 80° C., depending on the reactivity of the alkylating agent.

To be able to be eventually used as a suitable contrast agent comprising gadoterate meglumine, the concentrations of process impurities present in the raw DOTA (both organic and the inorganic) must be removed or significantly reduced. This is so that the purified DOTA meets the strict specifications for use in a contrast agent or else it will not be approved for sale by the relevant medicine regulatory body as it will not be considered safe enough for human use. Therefore a series of purification steps must be employed to remove these impurities without introducing too high a concentration of a new impurity or residual solvent, as these must also meet the specifications.

However, the DOTA resulting from the above mentioned processes is still highly contaminated with organic and inorganic impurities, in particular with chloride and sodium ions, and the conventional purification steps using ion-exchange resins, as disclosed above, only solves this problem in some extent.

In fact, G. Hernandez, M. F. Tweedle and R. G. Bryant, *Inorg. Chem.*, 1990, 29, 5109-5113, disclose the synthesis of the sodium salt of [Gd(DOTA)(H$_2$O)]$^-$ (Na[Gd(DOTA)(H$_2$O)].4H$_2$O). However, this compound is unsuitable for use as a contrast agent as it contains sodium. Nevertheless, the synthetic procedure herein disclosed highlights that high temperatures (90° C.) and long reaction times (6.5 hours) are required to successfully react DOTA and gadolinium oxide (Gd$_2$O$_3$, an ionic salt which is the source of the gadolinium ion) together to form the thermodynamically stable [Gd(DOTA)(H$_2$O)]$^-$. This can be accounted for by the very slow kinetics of formation of the complex.

It is thus desirable to obtain an optimized process for the raw DOTA synthesis which ensures not only high yields of this compound, at least 50% relative to the amounts of starting reagents used, but also that the raw DOTA is of a suitable quality and in a form that was easy to work with. Furthermore, it is also desirable to simplify the method for producing DOTA at an industrial scale.

SUMMARY OF THE INVENTION

Preferred embodiments of the present invention provide a method for preparing DOTA that allows obtaining high yields with an improved quality and purity in a simple, straightforward and reliable process.

The preferred embodiments are realised by providing a five-step process for preparing DOTA as defined below.

Other preferred embodiments of the invention provide a process for producing macrocyclic compounds comprising DOTA and metal ions complexes, as defined below.

Other preferred embodiments of the present invention provide a process for producing compositions comprising said macrocyclic compounds that can be used as contrast agents in magnetic resonance imaging.

Further advantages and embodiments of the present invention will become apparent from the following description and the dependent claims.

DETAILED DESCRIPTION OF THE PREFERRED EMBODIMENTS

The present invention relates to a four-step process for producing 1,4,7,10-tetraazacyclododecane-1,4,7,10-tetraacetic acid (DOTA), including salts and hydrates thereof of formula (I):

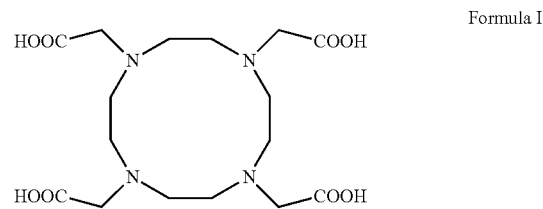 [SMILES: O=C(O)CN1CCN(CC(=O)O)CCN(CC(=O)O)CCN(CC(=O)O)CC1]

Formula I

The process of a preferred embodiment of the present invention comprises the following steps:

a) reacting the cyclen 1,4,7,10-tetra-azacyclododecane and a halo-acetic acid with a base at a pH≥10;

b) crystallizing the 1,4,7,10-tetraazacyclododecane-1,4,7,10-tetra acetic acid obtained in step a) by addition of an acid to achieve a pH≤3, followed by a heating step and cooling step, wherein the heating step is performed at a temperature in the range from 50° C. to 100° C., for at least 5 minutes, and the cooling step is performed at a temperature in the range from 5° C. to 25° C., for at least 5 minutes;

c) treating the raw material obtained in b) with a cationic resin and then desorbing DOTA with a volatile base solution;

d) further treating the resulting solution of c) with an anionic resin;

e) washing the product of d) in a two-stage wash, first with an organic volatile acid with a pKa less than 5 until DOTA starts to be released from the resin, and a second stage with an organic volatile acid with a pKa less than and/or with a higher concentration than the first selected organic volatile acid to release DOTA from the resin.

1. Synthesis of Raw DOTA

In the first step, cyclen (1,4,7,10-tetraazacyclododecane) is reacted with a halo-acetic acid and an excess of a base, at a pH≥10 according to the following reaction:

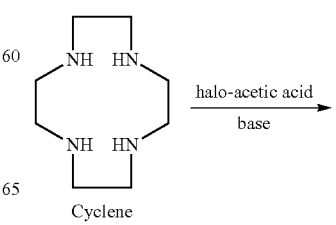

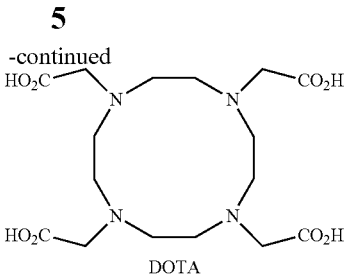

DOTA

The four amine groups on the cyclen molecule react with four equivalents of a halo-acetic acid in a nucleophilic substitution reaction.

In a preferred embodiment of the present invention halo-acetic acid means a derivative of acetic acid by substitution of one H by iodo, bromo or chloro. In a preferred embodiment chloroacetic acid is used.

An excess of a halo-acetic acid can be used in this step, preferably in an amount of at least 4 equivalents (eq.) and more preferably between 5.0-6.0 eq. with regard to the initial amount of cyclen.

According to the cited prior art, this step is performed at a temperature of approximately 80° C. However, it was found that using an excess of halo-acetic acid according to preferred embodiments the present invention, lower temperatures may be used. Therefore, in a preferred embodiment of the present invention, this step can be performed at a temperature ranging from 20 to 100° C., preferably from 20 to 65° C. and more preferably from 20 to 30° C.

The higher temperatures (≥65° C.) can be used to speed up the rate of reaction but they are less preferred in industrial processes due to the associated higher costs. Moreover, the yield of DOTA is not better than the one obtained at temperatures ranging from 20 to 65° C.

At the prior art temperatures, this step can be performed during around 40 h. Said reaction times (40 hours or more) can be used to ensure that all four amine groups undergo substitution and no tri-, di-or mono-substituted cyclen derivatives are present in the reaction mixture at the end. However, it was found that the maximum selectivity for product formation, according to a preferred embodiment of the present invention, is achieved after 20-24 h of reaction. Therefore, this step is also preferably performed during at least 7 h, most preferably at least 20 h, even more preferably at least 24 h.

As in the prior art, the reaction can performed at pH values of about 10. However, it was now surprisingly found that even when the reaction was performed at a pH≥13 no adverse effects were observed. By not having to constantly monitor the pH ~10 as described in the prior art, the synthesis procedure is easier to operate. Therefore, in a preferred embodiment of the present invention, this step of DOTA synthesis is performed at a pH≥13 by addition of a base at once with no "on process" monitoring of the pH values.

In a preferred embodiment of the present invention, suitable bases are inorganic bases such as hydroxides of alkali metals, and more preferably hydroxides of alkali metals selected from the group of KOH, NaOH, LiOH, RbOH and CsOH. In a most preferred embodiment of the present invention NaOH is used as a base.

The base can be added in excess, of at least 2 times the amount of the halo-acetic acid present in the reaction, namely by using amounts ranging from 8 to 16 equivalents, preferably between 10-12 equivalents with relation to the halo-acetic acid. Higher amounts of said base may be used but then larger amounts of cations are introduced into the system making their removal, in a later stage of the process, more difficult and consequently more difficult to achieve a better purification of DOTA. Furthermore, by using the above mentioned amount of base it is also possible to prevent the reaction from being too exothermic, which would be unsafe, especially on a large scale. The base can be added in solid form or as a concentrated solution, e.g. of at least 30%. A possible explanation for this is that the base activates the cyclen towards nucleophilic substitution and the resulting carboxylic acid pendant arms are also deprotonated under the basic conditions, resulting in the fully deprotonated DOTA molecule ($L^{4-}$, L referring to the ligand DOTA in its neutral form) with positive counterions.

The process of preferred embodiments of the present invention thus provide a first step which is easier to operate and takes less time than the ones of the prior art. Moreover, it also ensures that no undesirable side compounds are produced thus resulting in higher yields of raw DOTA.

2. Crystallization of Raw DOTA

During the second step, the reaction mixture is crystallized by addition of a concentrated acid and by performing a heating and cooling step, preferably followed by a washing step.

The acid is added until a pH≤3 is achieved producing a precipitate. Suitable acids are inorganic acids and more preferably acids selected from the group of HCl, $H_2SO_4$, $HNO_3$, HBr, HI and $HClO_4$.

The reaction is then subjected to a heating and cooling step to obtain an improved yield and quality of the crude DOTA. This is performed by heating the reaction at a temperature ranging from 50 to 100° C., preferably 50 to 70° C., more preferably 50 to 60° C., for a short time period of at least 5 minutes, in order to dissolve the precipitate and obtain a clear solution. Then the reaction is cooled at a temperature ranging from 5 to 25° C., preferably 5 to 15° C., more preferably 5 to 10° C., for a short time period of at least 5 minutes, to obtain DOTA in the form of a salt, such as DOTA hydrochloride or other salt, depending on the acid selected for lowering the pH of the solution.

Thus, this heating/cooling step allows to obtain the DOTA with a low content of other cations. In fact, it was surprisingly found that at pH~3 DOTA can be precipitated from the solution as a solid. The final pH of the reaction mixture is then low and can be less than 0.5. At this low pH values the raw DOTA is found in its fully protonated form ($H_6L^{2+}$) wherein L refers to the deprotonated ligand DOTA and whereby the counterions, such as chlorides, introduced by the reaction with the acid, are electrostatically bound to it, so that its form can be expressed as $H_6L(Xn^-)_{2/n}$, X refers to the counterions and n refers to the charge of the counterion. By precipitating DOTA as a salt it is easier to isolate it by filtration and to perform further purification. Apart from the negative counterions the raw DOTA is also contaminated with any residual ions introduced by the reaction with the base that precipitate out alongside the DOTA salt.

Preferably, a washing step is performed after the heating/cooling step to further remove the remaining cations. This can be done with a mixture of water and a water miscible low boiling organic solvent in a ratio ranging from 1:1.5 to 1:3, preferably in a ratio of 1:2 (weight/weight). Suitable examples of a water miscible low boiling organic solvent are acetone, ethanol, methanol and iso-propanol. In a preferred embodiment of the present invention, acetone or ethanol are used. Due to the low solubility of DOTA in such solvents this step is performed to precipitate DOTA from a solution in water.

The potential organic impurities present in the raw DOTA include any unreacted alkylating acid or intermediate cyclen derivatives. However, it is observed that the reaction goes to completion; the yield losses are most probably due to solubility issues, i.e. the DOTA failing to precipitate out of solution completely. It is possible to improve the yield of raw DOTA by adjusting the reaction conditions, but this affects adversely and significantly the purity and thus the synthetic method of a preferred embodiment of the present invention aims to achieve a compromise between yield and purity necessary to comply with the requirements for contrast agents.

In this way a raw DOTA can be obtained that has already a low cation content (<0.5%), which makes further purification easier. Also unreacted starting material, such as the halo-acetic acid that is in excess, and intermediates are removed. This also leads to a very pure final product and to yields of approximately 70%. The composition of the washing mixture is optimized for minimal loss of DOTA and low sodium content. Moreover, working at low pH values the reaction is easier to operate since no exact final pH is required.

3. Purification of DOTA 3.1. Treatment With Cationic Resin

The raw DOTA is first treated with a cationic resin to remove non desirable anions introduced by the addition of the acid in step b) of the process, such as chloride ions.

The cationic resin is typically a strongly acidic cationic exchange resin such as Amberlite IR120H, Lewatite S100H, or Purolite UCW9126 H+, preferably a resin in the hydrogen form due to its ready availability and good theoretical total capacity (2.0 meq/ml).

The positively charged raw DOTA and the cations are adsorbed by the resin while the anions remain in solution and can be washed away. To desorb the DOTA from the resin though requires the use of a volatile base in an aqueous solution so it can be easily removed and to increase the solution pH to values higher than 4. In a preferred embodiment of the present invention, a suitable volatile base may be ammonia, butylamine, triethylamine or diethylamine, ammonia being the preferred one.

Adding an aqueous volatile base to desorb the DOTA from the resin causes the remaining cations from the previous step and ions introduced by said volatile base to enter into equilibrium with one another. The relative selectivities favouring the adsorption of some cations to the resin are outweighed by the excess of the volatile base. This results in desorption of the cations from the cationic exchange resin during elution with aqueous base. The basic solution also raises the pH, resulting in converting the DOTA cationic salt into the neutral DOTA or even a DOTA anionic salt. Both these species will be released from the cationic exchange resin.

Desorbing DOTA as described introduces the volatile base ion as an impurity to the system, yielding for instance an ammonium-DOTA species as the major product from the treatment. The washing step with said volatile base may be repeated until no more DOTA is found in the solution.

Although not all the remaining cations resulting from the crystallization step can be removed during the ion exchange resin treatments, the concentration can be significantly reduced, particularly during the cationic resin treatment.

Therefore, the concentration of cations in the freshly synthesised raw DOTA can be sufficiently decreased, by the first 3 steps of the process of a preferred embodiment of the invention, before any further purification steps are performed and thus the product after the optimised ion exchange resin treatments meets the required sodium content specification. Using a larger volume of a concentrated acid was shown to help decrease the cation content of the raw DOTA. However, this step alone is insufficient for getting the desired low cation concentrations (around 0.1 w %), meaning that further purifications are needed.

Furthermore, the cationic exchange resin is a very effective treatment for removing the anions from the DOTA cationic salt so that the concentration present meets the specification without any further treatment required. It works regardless of the original concentration of anions in the raw DOTA because the anions simply do not bind to the cationic exchange resin (or remain electrostatically bound to DOTA) and can therefore be filtered and washed away off the DOTA-bound resin.

3.2 Treatment With Anionic Resin

The treated DOTA resulting from the previous step contains now the volatile base ions (~5%), which were introduced as an additional impurity to the system by the cationic resin treatment and thus must be substantially decreased. Therefore, the resulting DOTA is then subjected to an anionic exchange resin treatment to remove said impurities. On addition of the resin the negatively charged DOTA binds to the resin, freeing the said ions and other cations so that they can be washed away (the base ions and the hydroxide ions from the resin will be in equilibrium with base and water).

The anionic resin is typically a strong basic anionic exchange resin, such as Amberlyst A126OH, Lewatite M600OH or M800OH, Purolite UCW5072 OH—, preferably a resin in the hydroxide form due to its "ready-to-use" availability and good theoretical total capacity (1.0 meq/ml). 6 volumes of resin are used with regard to the weight of the cationic resin treated DOTA. If the content of DOTA in the solution is too high, an extra volume of resin may be added.

3.3 Washing With Organic Volatile Acids

After treating DOTA according to the procedure described in the previous step DOTA has to be released from the anionic resin. This is possible by converting it to the neutral or cationic form through the use of an acidic washing step.

Normally one would expect that by this step all cations should be removed as they do not bind to the anion exchange resin. However, it was found that after washing the resin with a volatile organic acid the obtained DOTA is still contaminated with cations introduced by the previous treatments. This might be explained by the fact that at the pH of the solution obtained after releasing DOTA from the cation exchange resin, said DOTA is at least partly in a di-anionic form $H_2L^{2-}$, where 1 charge is bound to a cationic resin site and the other charge is neutralised by an other cation that still is present in the solution after release from the cation exchange resin.

Thus, in order to avoid the problem of DOTA contamination with such cations, it was surprisingly found that the use of a two step washing, first with a more diluted solution of a chosen volatile acid washes away the cations from the DOTA-resin complex. In result, upon using a more concentrated acid, in the following second washing step, DOTA is released from the resin, possibly as a DOTA—formate or—acetate salt, the salt depending on the chosen volatile acid, but finally free from other cations.

Examples of suitable organic volatile acids for a preferred embodiment of the present invention are organic volatile acids with pKa less than 5, such as formic acid, acetic acid, and fluoracetic acid and oxalic acid. Formic acid and acetic acids are preferred being the most preferred the formic acid.

In a preferred embodiment formic acid or acetic acid is used. In a more preferred embodiment, formic acid is used because it introduces lower amounts of impurities that must be removed later.

If formic acid is used in the first washing step, a concentration between 0.01-0.1% may be used, preferably between 0.02-0.03%. If acetic acid is used in this step, then a concentration between 0.1-0.3% may be used. In a preferred embodiment of the invention, the organic volatile acid used in this step is formic acid.

In the second washing step, DOTA is released from the resin by addition of a higher concentration of the organic volatile acid used in the previous washing step or by adding an organic volatile acid with lower pKa than the one used in the previous washing step.

In a preferred embodiment, formic acid is used because it requires less effort in a later stage to obtain higher purity levels of DOTA but other acids may be used. In this sense, the formic acid concentration is between 0.5 and 20%, preferably between 1.0-5.0%, more preferably between 1.0-2.0% and even more preferably of 1.0%. The addition of a solution with higher concentrations of formic acid, such as 15-20% may speed up the procedure but it may also require further purification steps to remove impurities introduced in the system.

Therefore, lower amounts of said acids are needed to lower the pH of the mixture and thus fewer ions are introduced in the system resulting in an easier post treatment procedure for their removal in a later stage.

By following the above described washing procedure it was surprisingly found that it is possible to obtain good yields of DOTA in a high purified grade. This is mainly due first to the lower cationic content in the presence of the volatile base, probably due to a mass effect of excess of said base on the divalent anionic DOTA on the resin given by the first treatment with an organic volatile acid, and secondly due to the lower anionic content when a anionic resin was further eluted with an organic volatile acid in a higher concentration or at lower pH.

3.4 Concentration

The resulting DOTA fractions can be subsequently concentrated, by known techniques such as in a rotary evaporator under reduced pressure, and treated with water. This procedure can be repeated until a glassy oil is obtained, which can be further treated with a low boiling water miscible organic solvent such as ethanol or acetone to induce crystallisation. In the production plant, a powder can be obtained by concentrating to 10% by vacuum distillation and repeatedly adding the above specified solvent and concentrating again.

If the base content is still out of the required specifications the above obtained DOTA can be recrystallised by dissolving in water at a temperature above room temperature such as at 40-60° C. and precipitating with a water miscible low boiling solvent such as ethanol, acetone, cooling to room temperature, centrifuging and drying in a vacuum tray dryer.

4. Synthesis of Gadoterate Meglumine

The DOTA of high purity obtained as described above can be used as the ligand in the formation of the contrast agent gadoterate meglumine, [Gd(DOTA)(H$_2$O)](meglumine).

For this purpose, DOTA obtained according to a preferred embodiment of the present invention is added to Gd$_2$O$_3$ by known methods preferably with excess of DOTA, most preferably in a molar ratio slightly over 2:1 to form an aqueous solution of a complex DOTA-Gd.

5. Synthesis of a Contrast Agent Formulation

In order to prepare a contrast agent formulation, other excipients commonly accepted in pharmacy may be added to the gadoterate meglumine water solution. Typically the pH is adjusted to values tolerated by the body such as from 6.5 to 8.0.

DETAILED DESCRIPTION OF A PREFERRED EMBODIMENT

The present invention relates to a process for producing 1,4,7,10-tetraazacyclododecane-1,4,7,10-tetraacetic acid derivatives (DOTA), macrocyclic compounds comprising metal ions complexes thereof and compositions comprising said macrocyclic compounds, which can be used to produce contrast agents for magnetic resonance imaging.

1. Preparation of 1,4,7,10-tetraazacyclododecane-1,4,7,10-tetraacetic Acid (DOTA) Including Salts and Hydrates Thereof:

1.1 Synthesis of DOTA

Cyclen 1,4,7,10-tetra-azaclyclododecane and 5 to 6 eq. of chloroacetic acid (with regard to the initial amount of cyclen) are reacted with a base, such as NaOH at a pH≥13.

The chloroacetic acid is added to a solution of 1,4,7,10-tetraaza cyclododecane in water (5 to 15%, preferably 9-114 w/v) at a temperature ranging from 20 to 25° C. Then the reaction mixture is cooled to ~5° C. A base (in solid form or as a concentrated solution of at least 30%) is added slowly to the reaction mass by maintaining the internal temperature ~10° C. The reaction mass is then slowly warmed to ~25° C. and stirred for 20 to 24 h.

1.2 Crystallization of Raw DOTA

Crystallized DOTA is obtained by adding an acid, such as HCl, to the 1,4,7,10-tetraazacyclododecane-1,4,7,10-tetra acetic acid obtained in step a) to achieve a pH≤3, followed by an heating and cooling step. Preferably, a further washing step with a mixture of water and a water miscible low boiling organic solvent using a ratio of 1:1.5 to 1:3 is also performed.

The reaction mass obtained in the previous step is first cooled to a temperature of ~10° C., acidified with an acid to achieve a pH≤3 and stirred for 30 min producing a precipitated.

The slurry is slowly warmed to ~25° C. and heated to a temperature of 60-65° C. to obtain a clear solution and stirred for about 10 min. The reaction mass is slowly cooled to 5-10° C. and stirred for about 10 min. The slurry is filtered or centrifuged, suck dried for ~10 min and the bed was washed on the filter/centrifuge with a mixture of water and a low boiling water miscible solvent in a ratio of 1.5. The resulting solid is then suck dried for about 2 h and dried under vacuum conditions, such as in a tray drier, at 60±10° C. under diminished pressure until dry (for 6-12 h). The crude DOTA salt is thus obtained as a white powder in 70-80% yield and a content of about 80% by HPLC.

1.3 Purification of DOTA 1.3.1 Treatment With a Cationic Resin

The raw material obtained according to the previous step is further treated with a cationic resin followed by filtration, washing and desorbing with a diluted ammonia solution.

A cationic resin in its hydrogen form ready-to-use (6 volumes with respect to crude DOTA salt) is washed several times with water (about 15 volumes) until the supernatant attained a pH of 4.0-6.0.

The crude DOTA salt obtained in the previous step is dissolved in water (~10 volumes) and added to the pre-washed cationic resin, taken in the reactor and stirred at ~25° C. for 16 h, until the solution is free of DOTA. If necessary, an extra volume of resin is added to remove DOTA form the solution.

The resin is then washed with water (~15 volumes) several times until the supernatant attained a pH of 4.0-6.0. The resin is stirred with diluted aqueous solution of a volatile base (15-20 volumes, about 3%) for 10-20 min, allowed to settle for 20-30 min and the supernatant is collected separately. The same is repeated for some more times, ex. for 5 times, until no DOTA is observed in the supernatant. The product fraction is then collected together and concentrated to minimum volume (10 volumes with respect to crude DOTA), stripped-off with water (3 times 15 volumes) and the solution (10 volumes) is unloaded, rinsed the reactor with 5 volumes water and submitted for analysis to determine the DOTA assay. A small portion of the product is then completely concentrated and analyzed for ion content.

1.3.2 Treatment With Anionic Resin

The resulting solution of the previous step is treated with an anionic resin.

Thus, an anionic resin (6-7 volumes with respect to assay corrected cationic resin treated DOTA) is pre-treated by washing with water (about 6 times 15 volumes) until the supernatant to attain the pH 8.0-10.0.

The treated DOTA obtained in the previous section is then added to pre-washed anionic resin, taken in the reactor and stirred at ~25° C. for 4-6 h until the solution is free of DOTA. If necessary, an extra volume of resin is added to remove DOTA form the solution. The DOTA containing resin is washed with pure water (several times 15 volumes) until pH of the supernatant solution was 8-10.

1.3.3 Washing Step

After treating the resulting solution with an anionic resin a two-stage washing treatment is performed with organic volatile acids, first with an organic volatile acid at low concentration, and a second stage with a higher concentration of an organic volatile acid such as formic acid at 1-20% as preferred organic volatile acid.

Therefore, in the first washing step, the resin is stirred with about 20 volumes of a low concentration of an organic volatile acid, such as formic acid, for 20-30 min and allowed to settle for 10-15 min. Then the supernatant is removed. The same can be repeated for 1 to 2 times.

In the second washing step the resin is stirred with about 20 volumes of an aqueous solution of a volatile acid, such as formic acid, at 1-20% for 20 to 30 min, allowed to settle for 10 to 15 min and the supernatant is collected. The same can be repeated for several times (~5) until no DOTA is found in the supernatant. The supernatant is collected separately and checked for presence of DOTA by HPLC assay.

Preferably, the product fractions are concentrated to minimum volume (10 volumes with respect to cationic resin treated DOTA), stripped-off with water (4 times, 15 volumes), then stripped-off with low boiling water miscible organic solvent (3 times 6 volumes), cooled the reaction mass to ~25° C., a low boiling water miscible organic solvent is then added (8 volumes), cooled to ~10° C., stirred for 20 to 30 min at ~10° C. and centrifuged. The reactor is rinsed with a low boiling water miscible organic solvent (2 volumes), and the filtrate is bed washed with reactor rinsed the same low boiling water miscible organic solvent. The solid is suck dried for 30 min and dried under vacuum conditions at 60±10° C. for 6-12 h.

The obtained DOTA can be further purified by dissolving in water (5 to 10 volumes) at 40-60° C. and slowly adding a water miscible low boiling solvent (12-25 volumes). The slurry is stirred at ~25° C. for ~1 h, filtered and suck dried for ~3 h and dried, for example in a vacuum tray dryer at 50-70° C. for 6-12 h.

2. Synthesis of Gadoterate Meglumine

The DOTA of high purity obtained as described above can be used as the ligand in the formation of the contrast agent gadoterate meglumine, [Gd(DOTA)($H_2O$)](meglumine).

For this purpose, DOTA obtained according to a preferred embodiment of the present invention is added to $Gd_2O_3$ by known methods preferably with excess of DOTA, most preferably in a molar ratio slightly over 2:1 to form an aqueous solution of a complex DOTA-Gd.

The temperature of the reaction solution required to form DOTA-Gd complex was in the range from 80 to 120° C., preferably from 90 to 100° C., more preferably at a temperature of approximately 95° C.

As the kinetics of formation of the complex are very slow the reaction typically takes 2-8 h, preferably from 3-6 h, more preferably during approximately 4 h.

During this time the pH of the reaction solution typically decreases from ~3 to ~1.5-1.6. In order to chelate the Gd(III) ion DOTA must become fully deprotonated, which releases hydrogen ions into the solution. Due to its basic properties meglumine is then added after allowing the solution to cool to between 40 and 50° C. to balance the negative charge of the complex. Once protonated it electrostatically binds to the complex forming the meglumine salt and to increase the solution pH.

Meglumine is added until the pH of the solution is between 6.9-7.8, to meet the pH range required to allow the solution to be safely injected as contrast agent. Meglumine is used as an excipient in many drugs; however, it can be present in the final solution in excess because it can be well tolerated by the body. After stirring for about half an hour, to ensure the reaction has gone to completion, the reaction solution is then allowed to cool to room temperature and filtered.

The obtained filtrate was analysed by HPLC-MS and was found to contain gadoterate meglumine, showing that the quality of DOTA being synthesised can successfully be used to synthesise a solution of the contrast agent. The DOTA-Gd complex can be easily identified on the ESI mass spectrum from the collection of peaks 1 m/z value apart, centred at m/z 560. There are a number of $[M+H]^+$ peaks corresponding to the dehydrated complex because gadolinium has six stable isotopes, five ($^{155}Gd$, $^{156}Gd$, $^{157}Gd$, $^{158}Gd$ and $^{160}Gd$) of which all have relative abundances greater than 14%. Meglumine is also evident on the mass spectrum with a $[M+H]^+$ peak at m/z 196.

Measurements

1. In-Process Monitoring (IPC) of DOTA

The determination of content of 1,4,7,10-tetraaza-Cyclododecane was determined in process control samples by using reversed phase HPLC (High Performance Chromatography) with a gradient program and DAD (Diode Array Detection).

Chemicals and Reagents (As Listed or Equivalent):
Acetonitrile—HPLC grade
Water—HPLC grade or Milli-Q-ater
Orthophosphoric acid—HPLC grade
Potassium dihydrogen phosphate—AR grade
Instrumentation and Equipment (As Listed or Equivalent):
System: Agilent 1100/1200 series HPLC system with UV detector, or equivalent.
Pump: Constant flow HPLC pump capable of running a gradient
Detector: DAD detector
Data Acquisition: An electronic data acquisition system is required
Chromatographic Parameters:
Column: Prevail Organic Acid, (250×3.0)mm, 5.0 pm
Column Temperature: 30° C.
Detector Wavelength: 195 nm
Pump Configuration: Gradient
Flow rate: 0.44 mL/min
Injection Volume: 5 μL
Run Time: 40 min
Mobile phase A: 20 mM $KH_2PO_4$ in water at pH 2.5 using Diluent (see below)

Mobile phase B: Acetonitrile: Mobile phase A (60:40)
Mobile phase C: Acetonitrile: Water (60:40)
Mobile phase D: Acetonitrile: Water (90:10)
Diluent: 0.1% Orthophosphoric acid in water
Needle wash: Acetonitrile
Blank: Diluent
Gradient Table:

| Time (min) | Mobile phase, A (%) | Mobile phase, B (%) | Mobile phase, C (%) | Mobile phase, D (%) |
| --- | --- | --- | --- | --- |
| 0 | 100 | 0 | 0 | 0 |
| 10 | 100 | 0 | 0 | 0 |
| 20 | 50 | 50 | 0 | 0 |
| 21 | 0 | 0 | 100 | 0 |
| 24 | 0 | 0 | 100 | 0 |
| 25 | 0 | 0 | 0 | 100 |
| 32 | 0 | 0 | 0 | 100 |
| 33 | 100 | 0 | 0 | 0 |
| 40 | 100 | 0 | 0 | 0 |

System Suitability Preparation

Weigh about 100 mg of 1,4,7,10-tetraaza Cyclododecane, chloroacetic acid and DOTA standards into a 100 mL volumetric flask, dissolve and dilute to volume with diluent.
In Process Control Sample Preparation Weigh about 600 mg of DOTA sample into a 50 mL volumetric flask, dissolve and dilute to volume with diluent. (Prepare Test solution in Duplicate).
Retention Time:

| S. No. | Compound name | ~Retention time(min) |
| --- | --- | --- |
| 1 | DOTA | 4.6 |
| 2 | 1,4,7,10-tetraaza Cyclododecane | 2.7 |
| 3 | Chloro acetic acid | 6.9 |

2. Analysis for DOTA:
A. Purity and Assay (By HPLC)
Method Outline:

The method described above for In Process Control can be used for Purity and Assay determination.
B. Chloride and Formate Content (by IC)

This method was applied for the determination of Chloride and Formate content of DOTA sample by IC (Ion Chromatography).
Chemicals and Reagents:
Sodium bicarbonate: AR grade or equivalent;
Sodium carbonate: AR grade or equivalent;
Water: Milli Q grade or equivalent;
Sulphuric acid: AR grade or equivalent;
Instrumentation and Equipment:
System: 850 professional Ion chromatograph with auto sampler;
Detector: Conductivity detector
Preparations:
Eluent (3.2 mM Sodium Carbonate+1 mM Sodium Bicarbonate):

Weigh about 0.32 g of Sodium Carbonate and 0.084 g of Sodium bicarbonate in to a mobile phase bottle containing 1000 mL of milli-Q-water. Mix well, filter through 0.45μ filter and degas.
Suppressor Solutions (For Anions): 50 mM Sulphuric Acid Pipette out 2.8 mL of sulphuric acid in to a mobile phase bottle containing 1000 mL of milli-Q-water. Mix well, filter through 0.45μ filter and degas.
Chromatographic Parameters:
Column: Metrosep A Supp 5 (250/4) with guard column
Run Time: 30 min
Flow: 0.7 mL/min
Maximum pressure: 15 MPa
MSM: Active
Per. Pump: Rate 3
Temp. Coefficient: 2.3%/° C.
Injection volume: 20 μL
Column temperature: 25° C.
Preparation of Standard Stock Solution 1:

Weigh accurately 165.0 mg of sodium chloride and 106.0 mg of Formic acid into a 100 mL volumetric flask. Add about 10 mL of water and sonicate to dissolve and make up the volume with water. Mix well.
Preparation of Standard Stock Solution 2:

Pipette out 2.0 mL of this solution into 100 mL volumetric flask and make up to the volume with water.
Preparation of Test Solution (in Duplicate):

Weigh accurately 50 mg of sample into a 50 mL volumetric flask and make up the volume with water.
Inject the Following as Per the Sequence:

| S. No. | Sample information | No. of injections |
| --- | --- | --- |
| 1 | Blank[(water) | 1 |
| 2 | Standard solution | 5 |
| 3 | Blank(water) | 1 |
| 4 | Test solution-1 | 1 |
| 5 | Test solution- 2 | 1 |

Calculation of the content of anion by the following formula:

Using Peak area for quantification of chloride and formate content.

$$\text{Anion content (\% w/w)} = \frac{Asm \times Wst \text{ (mg)} \times 2 \times 50 \times AtWt \text{ of Anion} \times P}{Ast \times 100 \times 100 \times Wsa \text{ (mg)} \times \text{Mol wt salt } std \times 100}$$

Anion content (ppm) = Anion content in percentage × 1.000.000

Where,
Asm is area of the anion peak in the sample;
Ast is area of the anion peak in the standard;
Wst is the weight of the standard;
Wsa is the weight of the sample;
P is the potency of the standard;
AtWt of Anion is the atomic weight of the anion;
Mol wt. salt std is Mol in weight of the salt used as standard
C. Ammonium Content by IC:
Method Outline:

This method is applicable to determine the content and presence of ammonium ion of DOTA sample. This method uses reverse phase ion exchange chromatography.
Chemicals and Reagents (as Listed or Equivalent):
Dipicolinic acid: AR grade
Water: Milli-Q-Water;
Nitric acid: AR grade
Instrumentation and Equipment (as Listed or Equivalent):
System: Metrohm, model 850 compact IC
Pump: Constant flow pump
Detector: Conductivity detector
Data Acquisition: An electronic data acquisition system is required Chromatographic Parameters:
Column: Metrocep C-4 (4.6×250) mm ×4.0μ, Serial No. 1080.3137
Column temperature: 25° C.
Detector: Conductivity detector
Pump configuration: Isocratic
Flow rate: 0.6 mL/min
Injection volume: 20 μL
Run time: 40 min
Mobile phase: 1.7 mM Nitric acid and 0.7 mM Dipicolinic acid in water
Diluent: Water
Preparations:
Mobile Phase: 1.7 mM Nitric Acid and 0.7 mM 2,6-Dipicolinic Acid in Water
Weigh accurately about 0.12 g 2,6-Dipicolinic acid in to 1.0 L of Milli-Q water and add 0.15 mL of concentrate Nitric acid (67-69% w/w) into it, sonicate to dissolve and filter through 0.45μ membrane filter.
Preparation of Stock Solution:
Weigh accurately 370 mg each of ammonium formate into 100 mL volumetric flask dissolve and dilute with diluent up to the mark.
Preparation of Standard:
Pipette out 1.0 mL of above stock solution in to a 100 mL of standard volumetric flask and dilute with the diluent up to the mark.
Preparation of Test Solution (Duplicate):
Weigh accurately 50 mg of sample into a 50 mL volumetric flask and make up the volume with water.
Sequence Table:
Equilibrate the HPLC system and column with mobile phase and inject 10 μL of the solution as per the below sequence table.

| Sequence | Sample | No. of injection |
|---|---|---|
| 1 | Blank[(water) | 1 |
| 2 | Standard solution | 5 |
| 3 | Blank(water) | 1 |
| 4 | Test solution-1 | 1 |
| 5 | Test solution-2 | 1 |

Calculate the Content of Cation by the Following Formula $$\text{Cation content } (\% \text{ w/w}) = \frac{Asm \times Wst \text{ (mg)} \times 1 \times 50 \times AtWt \text{ of cation} \times P}{Ast \times 100 \times 100 \times Wsa \text{ (mg)} \times \text{Mol wt salt } std \times 100}$$

Cation content (ppm) = cation content in percentage × 1.000.000

Where,
Asm is area of the Ammonium (Cation) peak in the sample;
Ast is area of the cation peak in the standard;
Wst is the weight of the standard;
Wsa is the weight of the sample;
P is the potency of the standard;
AtWt of cation is the atomic weight of the cation; and
Mol wt. salt std is Mol in weight of the salt used as standard
Results are reported in weight per weight percentages.
D. Sodium Content (By ICP):
ICP -OES (Inductively Coupled Plasma—Optical Emission Spectrophotometry).
Results are reported in weight per weight percentages.

EXAMPLES

All reagents used in the following examples were readily available from commercial sources unless otherwise specified.
All reagents used to prepare DOTA and gadoterate meglumine, including 1,4,7,10-tetraazacyclododecane (cyclen), $Gd_2O_3$ and N-methyl-D-glucamine (meglumine), were obtained commercially and used as received.
All ion exchange resins used were obtained commercially and used as received unless otherwise stated in the experimental.
Amberlite IR120H was obtained from Fluka;
Purolite UCW9126H+ from Purolite;
Amberlyst A26OH obtained from Fluka;
Lewatit M800OH from Lanxess;
Purolite UCW5072 OH from Purolite;
Lewatit MonoPlus M 600 resin was obtained from Lanxess in the chloride form and converted to the hydroxide form by stirring 5 L of the resin in 12 L of 1M NaOH for 1 hour, washing extensively with deionised water and then repeating the process once more.
Aqueous solutions of NaOH (29 w %), HCl (36 w %), $NH_3$ (25 w %), HCOOH (85 w %) and $CH_3COOH$ (99 w %) were obtained commercially and diluted using deionised water as required.
In Process Control (IPC) using HPLC, according to the previous section (measurements): area percentages of the peaks, with regard to total peak area, are used to report values for cyclen as starting material and Dota as product. For the raw DOTA, yield is reported as the number of moles of isolated product (DOTA bis hydrochloride, without correcting for assay) per number of moles of cyclene starting material.
For purification steps, the yield is reported as the weight of isolated pure Dota per weight of crude DOTA input.
HPLC purity is reported according to the method described in the measurements section, using a standard sample of DOTA (obtained according to the International Conference on Harmonisation (ICH guidelines), unless otherwise stated.

Example 1

Kinetic Study for DOTA Production During the Step a) of the Process

This example illustrates the kinetics of step a) of the process for production of DOTA according to a preferred embodiment of the present invention. The reaction was conducted for 72 h at a temperature of 25° C., using chloroacetic acid as the halo-acetic acid (4.3 eq.) and sodium hydroxide as a base (11.0 eq.) in water (12×-12 parts of water for 1 part of initial amount of cyclen in weight) and samples were taken at different times for in-process control analysis via HPLC-chromatography (see above).
The results are shown in Table 1 as surface area % in the HPLC chromatograms and the conversion value (%) is found according to the following formula:

$$\text{Conversion } (\%) = 100\% - X$$

wherein X is the amount of cyclen.
Measured impurities comprise unreacted alkylating acid, intermediate cyclen derivatives and counterions introduced by the halo-acetic acid and by the treatment with a base.

TABLE 1

Kinetic study data

| Species | RRT* | \multicolumn{9}{c}{Reaction time (hours)} |
| --- | --- | --- | --- | --- | --- | --- | --- | --- | --- | --- |
| | | 0 | 1 | 3 | 5 | 7 | 20 | 26 | 50 | 72 |
| Cyclene | 0.101 | 15.40% | 4.31% | 0.79% | 3.46% | 1.09% | 0.85% | 0.00% | 0.00% | 0.00% |
| Impurity-1 | 0.116 | 17.56% | 15.19% | 5.12% | 0.00% | 1.63% | 0.29% | 0.00% | 0.00% | 0.00% |
| Impurity-2 | 0.149 | 11.97% | 24.82% | 8.04% | 5.84% | 0.39% | 0.10% | 4.26% | 4.39% | 3.01% |
| Impurity-3 | 0.201 | 0.00% | 13.05% | 0.00% | 0.00% | 0.00% | 0.00% | 6.53% | 1.60% | 4.78% |
| Impurity-4 | 0.224 | 8.06% | 7.86% | 34.45% | 31.00% | 27.07% | 12.31% | 4.90% | 3.92% | 1.79% |
| Impurity-5 | 0.329 | 7.09% | 9.85% | 16.37% | 18.13% | 20.59% | 16.66% | 19.53% | 16.82% | 13.71% |
| Impurity-6 | 0.424 | 0.270% | 0.17% | 0.27% | 0.28% | 0.29% | 0.27% | 0.23% | 0.00% | 0.00% |
| Impurity-7 | 0.604 | 0.440% | 1.11% | 0.00% | 0.00% | 0.00% | 0.00% | 0.00% | 0.00% | 0.00% |
| $ClCH_2CO_2H$ | 0.637 | 38.70% | 19.63% | 11.59% | 9.44% | 7.71% | 2.97% | 2.35% | 0.00% | 0.00% |
| DOTA | 1.000 | 0.52% | 4.02% | 23.31% | 31.76% | 41.23% | 64.29% | 62.21% | 61.59% | 62.23% |
| Conversion | NA | 84.60% | 95.69% | 99.21% | 96.54% | 98.91% | 99.15% | 100.00% | 100.00% | 100.00% |

*RRT = Relative Retention Time

These results show that in the settled conditions the reaction is completed after 20 h, i.e at that time the conversion rate is 100%, which means that the starting material was completely consumed and therefore, that the process of a preferred embodiment of the present invention can be carried out at temperatures as low as 20° C.

Example 2

Influence of the Temperature on Quantity and Quality for DOTA Production in Step a) of the Process This example illustrates the temperature ranges useful in the process for obtaining DOTA, according to a preferred embodiment of the present invention. The reaction was conducted for 20 h at temperatures ranging from 20° C. to 100° C. and pH≥10, using chloroacetic acid as a halo-acetic acid (4.3 eq.) and sodium hydroxide as a base (11.0 eq.) in water (12×-12 parts of water for 1 part of initial amount of cyclen in weight). Samples were taken for evaluation on the reaction progress and the amounts of cyclen and DOTA were measured by HPLC.

The yield and the purity of isolated DOTA were measured and used respectively as indicators of quantity and quality of the product obtained in each experiment conditions, as shown in Table 2.

TABLE 2

Influence of the temperature on DOTA production

| Input Details | | IPC | | Isolated raw DOTA | |
| --- | --- | --- | --- | --- | --- |
| Experiment | Reaction Condition | Cyclen (%) | DOTA (%) | Yield % (uncorrected) | Purity (HPLC) % |
| 1 | 20° C. | 0.00% | 60.04% | 77.3% | 81.28% |
| 2 | 60° C. | 0.00% | 69.06% | (not isolated) | |
| 3 | 100° C. | 0.00% | 42.29% | 86.6% | 68.01% |

For the experiment at 100° C., the IPC after 6 h: Dota = 43.07%, Cyclene = 0%.

The results of Table 2 show that the process for producing DOTA, according to a preferred embodiment of the present invention, can be performed at temperatures from 20° C. and still good yields (≥70%) and good quality (≥80%) are obtained. In experiment 1, there was no cyclen left after 20 h of reaction and DOTA could be obtained in good yield an quality. At 100° C., the cyclen has already disappeared after 6 hours. However, the DOTA peak reached its maximum only at about 42%.

Higher temperatures, such as at 60° C. can accelerate the reaction achieving also good results in terms of yield but they also increase the costs of producing DOTA, particularly when industrial processes are concerned. Furthermore, higher temperatures result in longer times for the precipitation of the product after acidification.

Example 3

Influence of the Halo-Acetic Acid Amount on Time, Quantity and Quality for DOTA Production in Step a) of the Process Cyclen was reacted with different amounts of chloroacetic acid, as an example of halo-acetic acid, at 20° C. to check for the product formation selectivity (IPC), whilst the other production factors were maintained. The amount of chloroacetic acid is indicated in Table 3 as mole equivalents with regard to cyclen and varied between 4.3 eq as in the conventional process (COMP=Comparative), 5.0 eq., 6.0 eq. and 8.0 eq. The quantity and quality of DOTA was determined as described in the previous section, and shown in Table 3.

TABLE 3

Influence of the equivalents of chloroacetic acid on DOTA production

| Input Details | | | IPC | | Isolated raw DOTA | |
| --- | --- | --- | --- | --- | --- | --- |
| Experiment | $ClCH_2CO_2H$ | Reaction time | Cyclen (%) | DOTA Formation (IPC) | Yield % | Purity (HPLC) % |
| 1 | 4.3 | 72 h | 0.00% | 60.04% | 77.3% | 81.28% |
| 2 | 5.0 | 24 h | 0.00% | 67.18% | 87.4% | 82.10% |

TABLE 3-continued

Influence of the equivalents of chloroacetic acid on DOTA production

| Input Details | | IPC | | Isolated raw DOTA | |
|---|---|---|---|---|---|
| Experiment | ClCH$_2$CO$_2$H | Reaction time | Cyclen (%) | DOTA Formation (IPC) | Yield % | Purity (HPLC) % |
| 3 | 6.0 | 20 h | 0.00% | 60.80% | 83.7% | 83.14% |
| 4 | 8.0 | 20 h | 0.00% | 52.30% | 85.2% | 74.88% |

The reactions with 6 and 8 equivalents of chloroacetic acid, respectively experiments nr. 3 and 4, showed maximum selectivity after 20 h. These conditions afforded the good yield and high purity levels of isolated DOTA. In experiment 4, the purity was lower than the one obtained in reactions with lower amounts of halo-acetic acid. The reaction nr.2 showed short reaction time (~24 h) and produced the best DOTA yield with the highest purity level. Reaction nr.1 was the slowest (72 h) resulting in reasonable yield of DOTA with high purity level.

Therefore, results of Table 3 clearly show that it is possible to obtain good purity and yield values of isolated DOTA and that the best results are achieved when 5.0-6.0 eq. of chloroacetic acid are used.

Example 4

Influence of the Amount of the Base on Time, Quantity and Quality for DOTA Production in Step a) of the Process Cyclen was reacted with 4.3 equivalents of chloroacetic acid, using different amounts of NaOH, as an example of a base, at 20° C., in order to achieve pH values≥10 and evaluate the pH role on DOTA yield, whilst the other production factors were maintained. The amount of NaOH is indicated in Table 4 as mole equivalents with regard to cyclen. The quantity and quality of DOTA was determined as described in the previous section, and shown in Table 4.

TABLE 4

Influence of the amount of the base on DOTA production

| Input Details | | IPC | | Isolated raw DOTA | |
|---|---|---|---|---|---|
| Experiment | Base | Reaction time | Cyclen (%) | DOTA Formation (IPC) | Yield (%) | Purity (HPLC) % |
| 1 | NaOH 11 eq, solid addition | 24 h | 0.00% | 60.04% | 77.3% | 81.28% |
| 2 | NaOH 9 eq, solid addition | 65 h | 39.86% | 58.51% | 34.7% | 86.87% |
| 3 | NaOH 11 eq, liquid addition | 20 h | 0.00% | 65.20% | 86.6% | 87.12% |

Results of Table 4 show that using larger excess of the base (11 equivalents compared with 9 equivalents), and thus generating pH values above the prior art given values (~10) and particularly generating pH values above 13, has no adverse effects in what regards purity and yield of DOTA and therefore, the process can be developed at higher pH values. Adding the base as a 30% solution yields comparable results with solid addition.

The advantage of this is that since it is no longer necessary to keep strict control of pH values and the base is added all at once, this step is performed in a more easy and smooth manner. It was also possible to observe that the amount of base is dependent on the amount of halo-acetic acid and should be at least 2 equivalents of said base per mole of acid to achieve good yield and purity levels of DOTA.

Example 5

Influence of the Amount of the Acid on Quantity and Quality for DOTA Crystallization in Step b) of the Process This example illustrates the effect of adding an acid on the quality of crude DOTA, especially on the cation impurity-related content (Table 5).

Experiments were conducted on DOTA obtained according to step a) of the process of a preferred embodiment of the present invention and at 20° C. during 20/24 h. In the prior art process, HCl was used to acidify the reaction mass to pH of 2-2.5. Several reactions were conducted with different amounts of concentrated hydrochloric acid (7.3, 9.3, 11.4, 15.6, 20.7, 31.1 equivalents respectively with regard to cyclen).

TABLE 5

Influence of different ratios of concentrated acid on the quantity and quality for DOTA crystallization

| Input Details | | Isolated raw DOTA | | | |
|---|---|---|---|---|---|
| Exp | HCl (eq.) | yield % | Purity (HPLC) % | Na$^+$ % | Cl$^-$ % |
| 1 | 7.3 | 79.40% | 87.48% | 4.76% | 12.60% |
| 2 | 9.3 | 86.60% | 83.40% | 0.52% | 20.43% |
| 3 | 11.4 | 83.00% | 82.58% | 0.52% | 19.52% |
| 4 | 15.6 | 79.40% | 84.04% | 0.35% | 19.01% |
| 5 | 20.7 | (101.10%) | 37.81% | 14.98% | 46.44% |
| 6 | 31.1 | (144.40%) | 42.53% | 32.03% | 65.71% |

The results of Table 5 show that in the conditions of experiments 1 to 4, respectively with 7.3, 9.3, 11.4 and 15.6 eq. of HCl, is possible to obtain crystallized DOTA with low contents of Cl$^-$.

Table 5 also shows that in the conditions of experiments 2 to 4, respectively with 9.3, 11.4 and 15.6 eq. of HCl, it is possible to obtain crystallized DOTA with particular low contents of Nat. The yields in the tables are not corrected for contaminants, this explains the figures of more then 100% for the items 5 to 7.

It is also clear, from Table 5, that when increasing or decreasing the HCL concentration results in higher sodium content in the crude DOTA. Furthermore, it is possible to observe that increases in HCL above 15.6 eq. result in higher chloride content and decrease the purity of crude DOTA.

Thus, by using values of HCL ranging from 9.3 eq. to 15.6 eq. it is possible to obtain crystallized DOTA with low sodium content and good purity (above 80%).

Example 6

Effect of Heating and Cooling the Reaction Mixture During the Crystallization Step on the Quantity and Quality DOTA This example illustrates the effect of heating and cooling the reaction mixture on the yield and quality of crude DOTA (Table 6).

The reaction was carried out with 5.0 equivalents of chloroacetic acid as the halo-acetic acid and 11.0 equivalents of NaOH as the base at 20° C. during 20/24h. In experiments 2, 3 and 4, the slurry, containing precipitated solid after acidifying to pH 0.5, was heated to obtain a clear solution at a temperature of 65° C., which was then slowly cooled and stirred for 10 min at 5° C. The precipitated solid was filtered and taken forward for further purification. Experiment 1 was performed without the heating/cooling step.

TABLE 6

Effect of the heating and cooling step on DOTA quantity and quality

| | IPC | | Isolated raw DOTA | | | |
|---|---|---|---|---|---|---|
| | (HPLC - area %) | | | Purity | | |
| Exp. | Cyclen (%) | Dota (%) | Yield % | (HPLC) % | Na+ % | Cl− % |
| 1 | 0% | 59.6% | 91.00% | 75.72% | 6.6% | 24.4% |
| 2 | 0% | 67.79% | 90.20% | 83.34% | 1.15% | 18.21% |
| 3 | 0% | 68.61% | 86.60% | 85.13% | 1.57% | 17.57% |
| 4 | 0% | 67.13% | 81.90% | 83.89% | 1.57% | 16.47% |

These results show that by performing the heating and cooling step during the crystallization of DOTA the quality of the crude DOTA obtained was better, in comparison to the crude DOTA obtained using the conventional procedure, where no heating/cooling process was performed, as HPLC purity (determined by area %) was higher and both sodium and chloride were lower.

Example 7

Effect of Heating and Cooling Step for Longer Times During the Crystallization Step on the Quantity and Quality DOTA The previous experiment was repeated with different times for the cooling and heating step in order to investigate whether is was possible to obtain even better results for the crude DOTA yield.

The reaction was heated to 65° C. during different times, then cooled to 5-10° C. or to temperatures below 0° C., at different times, and the slurry was then filtered, dried and the results measured (Table 7).

TABLE 7

Effect of the heating and cooling step for longer times on DOTA quantity and quality

| | | Isolated raw DOTA | | | | |
|---|---|---|---|---|---|---|
| Exp | Conditions | Purity (HPLC) | Na+ (%) | Cl− (%) | Yield (%) | Remarks |
| 1 | Heating: 65° C. for 2 h Cooling: 5-10° C. for 10 min | 81.46% | 3.17% | 12.84% | 78% | Effect of long time heating |
| 2 | Heating: 65° C. for 5 min Cooling: 5-10° C. for 2 h | 70.02% | 2.71% | 13.73% | 84% | Effect of long time cooling |
| 3 | Heating: 65° C. for 10 min Cooling: −5 to 0° C. for 10 min | 66.97% | 1.23% | 16.20% | 100% | Effect of short cooling at <0° C. |
| 4 | Heating: 65° C. for 10 min Cooling: 25° C. for 30 min | 81.04% | 1.3% | 11.39% | 67% | slurry stirred at RT |
| 5 | Heating: 65° C. for 10 min Cooling: 10° C. for 10 min | 83.56% | 0.58% | 16.25% | 93% | slurry stirred at 10° C. |

The results of Table 7 show that heating or cooling the reaction mixture for longer duration decreases the purity of the obtained crude DOTA. Similar results were obtained with stirring at RT (room temperature) for longer times.

When heating the reaction for longer times (≈2h), whilst maintaining the cooling procedure, similar purities are obtained showing that there is no benefit on prolonging the heating period (comparison between Exp. 1 and 5).

When cooling the reacting for longer times (≈2h), whilst maintaining the heating procedure, lower purities are obtained (comparison between Exp. 2 and 5).

When cooling the reaction with higher temperatures (≈25° C.), whilst maintaining the heating procedure, similar purities are obtained (comparison between Exp. 4 and 5) but the yield is higher at the lower temperature.

When cooling the reaction with even lower temperatures (≈5° C.), whilst maintaining the heating procedure, lower purities are obtained (comparison between Exp. 3 and 5).

The procedure by heating at 65° C. for a short period of time (~15 minutes) followed by a cooling step at 10° C. during 10 minutes (Exp. 5) gives the best results in terms of yield (2.58 g/g cyclene) and quality (assay 85.36%, Na+ 0.58%).

Example 8

Treatment with a Cationic Resin

This example illustrates the role of treating the crystallized DOTA with a cationic resin to reduce the content of anion impurities (Table 8).

The crude DOTA obtained in the previous steps was dissolved in 10 volumes water and adsorbed onto pre-washed cationic resin Amberlite IR-120 (Fluka) at 20° C. during ~16 h. The resin was washed with water until a pH of 4.5-6.0 (supernatant) was attained. Then the resin was washed with 3% aqueous ammonia solution (6×4 volumes with respect to crude DOTA). The product fractions were concentrated and dried to yield 75-85% DOTA.

TABLE 8

Treatment with cationic resin

| | Input (Raw Dota) | | | Output (purified Dota) | | | | |
|---|---|---|---|---|---|---|---|---|
| Experiment | Na$^+$ | Cl$^-$ | Purity (HPLC) | Isolated yield | Na$^+$ | Cl$^-$ | NH$_4^+$ | Purity (HPLC) |
| 1 | 1.15% | 18.21% | 83.34% | 86% | 0.81% | 547 ppm | ND | 99.62% |
| 2 | 1.15% | 18.21% | 83.34% | 83% | 0.88% | 233 ppm | ND | 99.04% |
| 3 | 0.35% | 19.01% | 84.04% | 76.5% | 0.31% | 72 ppm | 2.80% | 98.89% |
| 4 | 135 ppm | 20.61% | 84.26% | 47% | 172 ppm | 355 ppm | 6.37% | 99.28% |
| 5 | 4801 ppm | 19.69% | 82.81% | 82.6% | 0.36% | 200 ppm | 5.67% | 99.66% |
| 6 | 112 ppm | 18.49% | 83.59% | 92.0% | 0.007% | 0.06% | 2.60% | 99.43% |
| 7 | 0.15% | 18.30% | 90.40% | 85.7% | 821 ppm | 0.05% | 2085 ppm | 99.04% |

The results of Table 8 show that the anion content of DOTA (chloride ion) was reduced to an acceptable limit (below 0.1%). Further reduction is realised in the next steps. However the treatment introduces ammonium ion into DOTA (as ammonia was used for elution) and sodium content is only marginally decreased proving that any cations must be removed in early stages of the process in order to achieve higher yields and the required purity of DOTA.

Example 9

Treatment with an Anionic Resin

This example illustrates the role of treating the obtained DOTA, as described in the previous step, with an anionic resin to reduce the content of ammonium impurities.

The cationic treated DOTA dissolved in 10 volumes water was adsorbed onto pre-washed anionic resin Amberlyst A26 OH at 20° C. during 4-6 h. The resin was washed with water to attain the pH 8-10 (supernatant), followed by washing with diluted aqueous formic acid solution as the preferred organic volatile acid to remove residual ammonium, followed by 1% aqueous formic acid solution. The product fractions were concentrated and dried (Table 9).

Details of the washing procedure are given in Example 10, Table 10.1.

These results show that the ammonium content was reduced within the acceptable required limit (below 0.1%). The level can be further reduced by recrystallizing in water/solvent if necessary. However, it introduced formate ion into the system (formate amount not presented). The yield obtained with this process was 80-99% and is possibly mainly influenced by the scale of the reaction. Better results are obtained when using higher amounts of reactants which are easier to be accurately measured.

Example 10

Effect of Dilute Volatile Acid Wash in the First Step of the Washing Procedure d) of the Process In experiments 2 and 3 in the previous example, the volatile acid (dilute) used in the first stage of the washing was formic acid and the concentration was 0.1% for Exp. 2 and 0.02% for Exp. 3. For the second stage of the washing, 1% formic acid was used also for the mentioned experiments. In experiment 4, the dilute volatile acid used in the first stage of the washing was acetic acid, 0.26%, calculated to have the same pH as the 0.02% formic acid. Details on the procedure are given in table 10.1.

TABLE 9

Treatment with an anionic resin

| | Input (H$^+$ resin purified Dota) | | | | Output (OH$^-$ resin purified DOTA) | | | | | |
|---|---|---|---|---|---|---|---|---|---|---|
| Exp | Na$^+$ | Cl$^-$ | NH4$^+$ | Purity (HPLC) | Yield % | Na$^+$ % | Cl$^-$ % | NH4$^+$ % | HCOO$^-$ % | Purity (HPLC) |
| 1 | 0.37% | 0.02% | 5.7% | 99.66% | 89% | 0.12% | 0.01% | 0.07% | 0.10% | 99.30% |
| 2 | 0.01% | 0.06% | 2.6% | 99.43% | 91% | 0.01% | 0.02% | 0.02% | 1.24% | 99.63% |
| 3 | 0.08% | 0.05% | 0.2% | 99.04% | 99% | 0.02% | 0.06% | 0.04% | 0.91% | 99.03% |
| 4 | | | 2.6% | | 91% | | | 0.0002% | | |

TABLE 10.1

| | | First wash | | | | Final wash | | | |
|---|---|---|---|---|---|---|---|---|---|
| Exp | Exp Of Table 9 | Vol. acid | Conc. | Number of washes | Wash volume (mL/g of DOTA) | Vol. acid | Conc. | Number of washes | Wash volume (mL/g of DOTA) |
| 1 | 2 | formic | 0.10% | 2 | 10 | formic | 1% | 7 | 10 |
| 2 | 3 | formic | 0.02% | 2 | 10 | formic | 1% | 8 | 10 |
| 3 | 4 | acetic | 0.26% | 2 | 25 | formic | 1% | 3 | 30 |

Procedure for anionic resin wash

For experiments 1 and 2 in table 10.1, the different fractions obtained from the first and second stages of the washing step were also analysed for DOTA content, to prove that the dilute volatile acid used in the first stage of the washing does not remove DOTA from the anionic resin. The result is presented in tables 10.2 and 10.3.

Samples of each stage of the washing step of the above mentioned experiments 1 and 2 were collected and analysed for DOTA content by HPLC. In both instances it is shown that the diluted formic acid washes used in the first step only remove minor quantities of DOTA from the resin. The second stage using higher concentration of the volatile acid releases the bulk of DOTA from the resin washing it out to the eluate. The releasing and washing of DOTA from the resin may continue during the several repetitions of the second stage until only a marginal amount of DOTA is present in the eluate.

TABLE 10.2

Exp. 1 from table 10.1

| Wash fraction | Formic acid conc | Dota conc HPLC (%) | DOTA recovered (% of total) |
|---|---|---|---|
| 1 | 0.10% | 0.00% | 0.00% |
| 2 | | 0.00% | 0.00% |
| 3 | 1.00% | 0.03% | 0.25% |
| 4 | | 2.54% | 21.51% |
| 5 | | 5.45% | 46.15% |
| 6 | | 2.53% | 21.42% |
| 7 | | 1.07% | 9.06% |
| 8 | | 0.16% | 1.35% |
| 9 | | 0.03% | 0.25% |

TABLE 10.3

Exp. 2 from table 10.1

| Wash fraction | Formic acid conc | Dota conc HPLC (%) | DOTA recovered (% of total) |
|---|---|---|---|
| 1 | 0.020% | 0.01% | 0.09% |
| 2 | | 0.03% | 0.30% |
| 3 | 1.00% | 0.29% | 3.15% |
| 4 | | 3.80% | 41.23% |
| 5 | | 2.90% | 31.47% |
| 6 | | 1.30% | 14.11% |
| 7 | | 0.60% | 6.51% |
| 8 | | 0.21% | 2.28% |
| 9 | | 0.06% | 0.64% |
| 10 | | 0.02% | 0.23% |

These results of Tables 10.2 and 10.3 show that the first stage of the washing step performed with 0.1% formic acid does not elute DOTA from the anionic resin—no product (DOTA) was detected in the eluate, thus only removes the ammonium.

The purified DOTA was obtained by elution from the resin only with higher concentrations of formic acid (1.0%) during the second stage of the washing step allowing to obtain good yield of DOTA as required to produce contrast agents.

Similar results were obtained when acetic acid was used in the first stage of the washing step instead of formic acid. The first stage was performed with 0.26% acetic acid (calculated to have the same pH as a 0.02% formic acid solution).

The invention claimed is:

1. A process for preparing 1,4,7,10-tetraazacyclododecane-1,4,7,10-tetraacetic acid (DOTA) or a salt or a hydrate thereof and having formula (I):

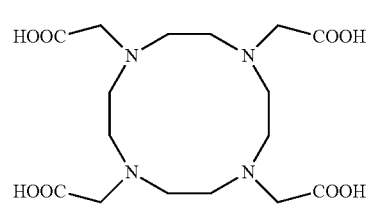

Formula (I)

the process comprising the steps of:
a) reacting 1,4,7,10-tetra-azacyclododecane and a haloacetic acid with a base at a pH ≥10 so as to obtain the DOTA;
b) crystallizing the DOTA obtained in step a) by adding an acid to achieve a pH ≤3, followed by a heating step and a cooling step, wherein the heating step is performed at a temperature in a range from 50° C. to 100° C. for at least 5 minutes, and the cooling step is performed at a temperature in a range from 5° C. to 25° C. for at least 5 minutes so as to obtain a raw material;
c) treating the raw material obtained in step b) with a cationic resin and then desorbing the DOTA with a volatile base solution;
d) further treating a solution resulting from step c) with an anionic resin; and
e) washing a product produced in step d) in a two-stage wash including a first stage with a first organic volatile acid with a pKa less than 5 until the DOTA starts to be released from the anionic resin, and a second stage with an organic volatile acid with a pKa less than or equal to the pKa of the first organic volatile acid and/or with a higher concentration than the first organic volatile acid to release the DOTA from the anionic resin.

2. The process according to claim 1, wherein step a) is performed at a pH ≥13.

3. The process according to claim 1, wherein an amount of the halo-acetic acid in step a) is at least 4 equivalents with regard to an initial amount of cyclen and an amount of the base is at least two times a number of equivalents of the halo-acetic acid.

4. The process according to claim 1, wherein the halo-acetic acid is selected from the group consisting of iodo-acetic acid, bromoacetic acid, and chloroacetic acid.

5. The process according to claim 1, wherein the base in step a) is an alkali metal hydroxide.

6. The process according to claim 1, wherein the acid added in step b) is selected from the group consisting of HCl, $H_2SO_4$, $HNO_3$, HBr, HI, and $HClO_4$.

7. The process according to claim 1, wherein the heating and cooling steps in step b) occur, respectively, at a temperature in a range from 50 to 60° C. and a temperature in a range from 5 to 10° C.

8. The process according to claim 1, further comprising performing a washing step with a mixture of water and a water miscible low boiling organic solvent selected from the group of acetone, ethanol, methanol, and iso-propanol in a ratio from 1:1.5 to 1:3 (weight/weight) between step b) and step c).

9. The process according to claim 1, wherein, in step e), the organic volatile acid used in the first stage is formic acid or acetic acid in an aqueous solution at a concentration between 0.01-0.1% or 0.1-0.3% respectively, and the organic volatile acid used in the second stage is formic acid in an aqueous solution at a concentration in a range from 1 to 20%.

10. A process for preparing gadoterate meglumine, the process comprising the steps of:
performing the process as described in claim 1;
f) adding $Gd_2O_3$ to the DOTA so as to form a DOTA-Gd complex; and
g) adding meglumine to the DOTA-Gd complex.

* * * * *